United States Patent
Rice et al.

(10) Patent No.: US 11,709,120 B2
(45) Date of Patent: Jul. 25, 2023

(54) SYSTEM FOR BLOOD FLOW MEASUREMENT WITH AFFIXED LASER SPECKLE CONTRAST ANALYSIS

(71) Applicant: Covidien AG, Neuhausen Am Rheinfall (CH)

(72) Inventors: Tyler Bywaters Rice, Santa Ana, CA (US); Sean Michael White, Santa Ana, CA (US); Bruce Yee Yang, Irvine, CA (US)

(73) Assignee: Covidien AG, Neuhausen am Rheinfall (CH)

( * ) Notice: Subject to any disclaimer, the term of this patent is extended or adjusted under 35 U.S.C. 154(b) by 719 days.

(21) Appl. No.: 16/091,054

(22) PCT Filed: Apr. 4, 2017

(86) PCT No.: PCT/US2017/025979
§ 371 (c)(1),
(2) Date: Oct. 3, 2018

(87) PCT Pub. No.: WO2017/176781
PCT Pub. Date: Oct. 12, 2017

(65) Prior Publication Data
US 2019/0086316 A1   Mar. 21, 2019

Related U.S. Application Data

(60) Provisional application No. 62/318,884, filed on Apr. 6, 2016.

(51) Int. Cl.
*G01N 15/02* (2006.01)
*G02B 27/48* (2006.01)
(Continued)

(52) U.S. Cl.
CPC ........ *G01N 15/0211* (2013.01); *A61B 5/0059* (2013.01); *A61B 5/0066* (2013.01);
(Continued)

(58) Field of Classification Search
CPC ... A61B 5/0059; A61B 5/0261; A61B 5/0075; A61B 5/0071; G01N 15/0211; G01F 1/7086
See application file for complete search history.

(56) References Cited

U.S. PATENT DOCUMENTS

| | | | |
|---|---|---|---|
| 7,737,959 B2 | 6/2010 | Gruhlke et al. | |
| 8,684,900 B2 * | 4/2014 | Tran | A61B 5/002 600/3 |

(Continued)

FOREIGN PATENT DOCUMENTS

| | | |
|---|---|---|
| CN | 1928801 A | 3/2007 |
| CN | 103300841 A | 9/2013 |

(Continued)

OTHER PUBLICATIONS

Bergstrand, Sara, et al. "Blood flow measurements at different depths using photoplethysmography and laser Doppler techniques." Skin research and technology 15.2 (2009): 139-147.*

(Continued)

*Primary Examiner* — Ashley K Buran
*Assistant Examiner* — Sean V Blinder
(74) *Attorney, Agent, or Firm* — Shumaker & Sieffert, P.A.

(57) ABSTRACT

Devices, systems, and methods are disclosed for improved laser speckle imaging of samples, such as vascularized tissue, for the determination of the rate of movement of light scattering particles within the sample. The system includes a structure adjoining a light source and a photo-sensitive detector. The structure can be positioned adjacent the sample (Continued)

(e.g., coupled to the sample) and configured to orient the light source and detector relative the sample such that surface reflections, including specular reflections and diffuse reflections, are discouraged from entering the detection field of the detector. The separation distance along the structure between the light source and the detector may further enable selective depth penetration into the sample and biased sampling of multiply scattered photons. The system includes an operably coupled processor programmed to derive contrast metrics from the detector and to relate the contrast metrics to a rate of movement of the light scattering particles.

60 Claims, 7 Drawing Sheets

(51) Int. Cl.
| | |
|---|---|
| A61B 5/026 | (2006.01) |
| G01F 1/7086 | (2022.01) |
| A61B 5/00 | (2006.01) |
| A61B 5/028 | (2006.01) |
| G01N 15/00 | (2006.01) |
| G01F 1/712 | (2006.01) |

(52) U.S. Cl.
CPC .......... *A61B 5/0071* (2013.01); *A61B 5/0075* (2013.01); *A61B 5/026* (2013.01); *A61B 5/028* (2013.01); *A61B 5/0261* (2013.01); *A61B 5/681* (2013.01); *A61B 5/6802* (2013.01); *G01F 1/7086* (2013.01); *G01N 15/0227* (2013.01); *G02B 27/48* (2013.01); *A61B 2562/0233* (2013.01); *A61B 2562/185* (2013.01); *G01F 1/712* (2013.01); *G01N 2015/0065* (2013.01); *G01N 2015/0222* (2013.01)

(56) References Cited

U.S. PATENT DOCUMENTS

| | | | | |
|---|---|---|---|---|
| 9,226,673 | B2* | 1/2016 | Ferguson, Jr. | ....... A61B 5/0044 |
| 9,241,635 | B2* | 1/2016 | Yuen | ................. A61B 5/02405 |
| 2005/0143662 | A1 | 6/2005 | Marchitto et al. | |
| 2008/0088853 | A1 | 4/2008 | Hwang et al. | |
| 2010/0056887 | A1 | 3/2010 | Kimura et al. | |
| 2011/0013002 | A1 | 1/2011 | Thompson et al. | |
| 2011/0026783 | A1 | 2/2011 | Fujii et al. | |
| 2013/0172691 | A1 | 7/2013 | Tran | |
| 2013/0245456 | A1 | 9/2013 | Ferguson, Jr. et al. | |
| 2013/0296715 | A1 | 11/2013 | Lasser et al. | |
| 2014/0052006 | A1 | 2/2014 | Lee et al. | |
| 2014/0135612 | A1 | 5/2014 | Yuen et al. | |
| 2014/0206976 | A1 | 7/2014 | Thompson et al. | |
| 2014/0206980 | A1* | 7/2014 | Lee | ..................... A61B 5/0261 |
| | | | | 600/407 |
| 2015/0105638 | A1 | 4/2015 | Eisen et al. | |
| 2016/0058309 | A1* | 3/2016 | Han | ..................... A61B 5/0261 |
| | | | | 600/479 |
| 2016/0058340 | A1 | 3/2016 | Ruchi et al. | |
| 2016/0059309 | A1 | 3/2016 | Han | |
| 2016/0231236 | A1* | 8/2016 | Gulati | ............... A61B 5/02433 |
| 2017/0181636 | A1 | 6/2017 | Luo et al. | |

FOREIGN PATENT DOCUMENTS

| | | | |
|---|---|---|---|
| CN | 105188523 A | 12/2015 | |
| CN | 105358052 A | 2/2016 | |
| CN | 105451640 A | 3/2016 | |
| WO | 2014197003 A1 | 12/2014 | |
| WO | WO 2015/022583 A2 | 2/2015 | |
| WO | WO 2015/176294 | 11/2015 | |
| WO | WO-2015176294 A1 * | 11/2015 | ........... A61B 5/6847 |

OTHER PUBLICATIONS

"Laser Speckle Contrast Imaging." Functional Optical Imaging Laboratory https://foil.bme.utexas.edu/research/laser-speckle-contrast-imaging (2014).*
Boas, David A., and Andrew K. Dunn. "Laser speckle contrast imaging in biomedical optics." Journal of biomedical optics 15.1 (2010): 011109.*
Electro-Optical Imaging Systems, https://fas.org/man/dod-101/navy/docs/es310/EO_image/EO_Image.htm (2000).*
Annemarie Nadort: "Glow with the flow: Quantifying blood flow and photoluminescence signal in biological tissue", Apr. 1, 2015 (Apr. 1, 2015), XP055621538; Retrieved from the Internet: URL:https://pure.uva nl/ws/files/2488561/158363_Nadort_thesis_complete.pdf [retrieved on Sep. 12, 2019].
Briers JD: "Laser speckle contrast imaging for measuring blood flow", Optica Applicata, Oficyna Wydawnicza Politechniki Wroclawskiej, PL, vol. 37, No. 1-2, Jan. 1, 2007 (Jan. 1, 2007), pp. 139-152, XP009101637, ISSN: 0078-5466.
Suzie Dufour et al: "Evaluation of laser speckle contrast imaging as an intrinsic method to monitor blood brain barrier integrity", Biomedical Optics Express, vol. 4, No. 10, Aug. 30, 2013 (Aug. 30, 2013), p. 1856, XP055621529, United States ISSN: 2156-7085, DOI: 10.1364/BOE.4.001856.
Extended European Search Report for PCT Application No. PCT/US17/25979, dated Sep. 25, 2019, in 15 pages.
Second Office Action and machine translation thereof, from counterpart Chinese Application No. 201780029605.5, dated Mar. 17, 2021, 19 pp.
Examiner Requisition from counterpart Canadian Application No. 3,018,567 dated Jan. 21, 2022, 5 pp.
Notice of Intent to Grant, and translation thereof, from counterpart Chinese Application No. 201780029605.5 dated Sep. 8, 2021, 3 pp.
Office Action from counterpart Canadian Application No. 3,018,567 dated Mar. 3, 2022, 5 pp.
Response to Examiner Requisition dated Jan. 21, 2022, from counterpart Canadian Application No. 3,018,567 filed Feb. 11, 2022, 2 pp.
Withdrawal of Examiner's Report from counterpart Canadian Application No. 3,018,567 dated Mar. 2, 2022, 1 pp.
Response to Office Action dated Mar. 3, 2022, from counterpart Canadian Application No. 3,018,567 filed Jun. 30, 2022, 22 pp.
Communication pursuant to Article 94(3) EPC from counterpart European Application No. 17779676.0 dated Oct. 18, 2022, 8 pp.
Federation of American Scientists (FAFS), "Electro-Optical Imaging Systems", 2000, 16 pp., (Applicant points out, in accordance with MPEP 609.04(a), that the year of publication, 2000, is sufficiently earlier than the affective U.S. filing date, so that the particular month of publication is not an issue.) (Downloaded from https://man.fas.org/dod-10/navy/docs/es310/EO_Image.htm) (2000).
Requisition from counterpart Canadian Application No. 3,018,567 dated Nov. 23, 2022, 5 pp.
International Search Report for PCT Application No. PCT/US17/25979, dated Jun. 21, 2017, in 2 pages.
Communication Pursuant to Rules 161(1) and 162 EPC dated Nov. 13, 2018 from counterpart European Application No. 17779676.0, 3 pp.
Communication pursuant to Rules 70(2) and 70a(2) dated Oct. 11, 2019, from counterpart European Application No. 17779676.0, 1 pp.
International Preliminary Report on Patentability from International Application No. PCT/US2017/025979, dated Oct. 9, 2018, 8 pp.
First Office Action and Search Report, and partial translation thereof, from counterpart Chinese Application No. 201780029605.5, dated Sep. 23, 2020, 14 pp.
Response to Communication pursuant to Article 94(3) EPC dated Oct. 18, 2022, from counterpart European Application No. 17779676.0, filed Feb. 16, 2022, 20 pp.
Response to Office Action dated Nov. 23, 2022, from counterpart Canadian Application No. 3,018,567 filed Mar. 22, 2023, 24 pp.

* cited by examiner

SYSTEM FOR BLOOD FLOW MEASUREMENT WITH AFFIXED LASER SPECKLE CONTRAST ANALYSIS

INCORPORATION BY REFERENCE

This application is a U.S. national stage application of International Patent Application No. PCT/US2017/025979, filed Apr. 4, 2017, which claims priority benefit of U.S. Provisional Patent Application No. 62/318,884, filed Apr. 6, 2016, which are incorporated herein by reference in their entirety for all purposes. Any and all applications related thereto by way of priority thereto or therefrom are hereby incorporated by reference in their entirety.

BACKGROUND

Field

Embodiments of the disclosure relate to novel methods, devices, and systems for performing optical, noninvasive measurements of the rate of movement of light scattering particles within a sample of interest. Particularly, the disclosure relates to devices, methods, and systems used to measure the volumetric flow and/or movement (e.g., diffusion) of light scattering particles by quantifying alterations in the interference pattern produced when the moving particles scatter light.

Description of the Related Art

The Dynamic Light Scattering (DLS) technique for determining particle size and flow rate in a solution can be performed in a variety of ways. One DLS method, called laser speckle imaging (LSI), uses a coherent laser source to illuminate a sample of light scattering particles, and images the scattered light using a multi-pixel detector (for example, a silicon-based camera sensor). The sensor records the so-called "speckle" pattern, produced by light interference, as the scattered coherent light recombines onto the detection element. If the scattering particles are in motion, the interference pattern will fluctuate over time. The detection element has a finite exposure time, and if the interference pattern fluctuates during the exposure, the speckles will "blur," or their light intensity will be averaged, within the detection elements. Researchers have previously developed a methodology to quantify the amount of "blurring" during the exposure by calculating the standard deviation of a local neighborhood of pixel intensities, often normalizing to the mean. This parameter is typically referred to as the "speckle contrast." A reduction in speckle contrast indicates an increase in motion (e.g., flow or diffusion) and vice versa. LSI is a useful technology in biomedical research to study blood flow within vascularized tissue. Cells and other structures within the blood scatter the coherent light as they flow through the vasculature, and LSI can quantify this flow.

One disadvantage to conventional LSI is its high susceptibility to motion artifact. Each imaging component and the sample are mounted independently to ensure proper alignment. The sample is often biological, and subject to movement independent of the camera and/or light source. When the sample moves independently of the imaging system, the motion from the movement is conflated with the motion of scatterers within the sample, causing erroneous results in the speckle image.

Another disadvantage to conventional LSI is susceptibility to surface reflections, shallow depth penetration (typically less than 1 mm), and low sampling of the dynamic particles within the sample relative to the total detected signal. Ideally, all detected photons will have scattered from dynamic particles (usually located within the sample). However, in traditional LSI, many photons undergo specular reflection from the sample surface, or scatter off static objects (e.g. epidermal skin) at the sample surface, called diffuse reflection. For example, specular reflection is the process by which a mirrored surface reflects light, whereas diffuse reflection is the process by which matte objects, such as a sheet of binder paper, reflect light. Shallow penetration and non-dynamic scattering events arise in large part due to the LSI system geometry, where the sample surface being imaged is also directly illuminated by the source. In this reflection geometry, light from the light source illuminates an area of the sample surface, herein referred to as the "area of illumination." If the surface is smooth, light may undergo mirror-like reflection off the sample surface within the area of illumination and enter the detector without interrogating the sample properties of interest (moving light scatterers such as red blood cells). If the surface is matte or rough (i.e. like white paper) light may undergo diffuse reflection on the sample surface within the area of illumination. Light that has undergone specular or diffuse reflection is generally not dynamically scattered by flowing particles, which are located beneath the surface, and therefore most likely does not contain any flow information. Specular and diffuse reflectance therefore causes undesirable signal content to be included in LSI measurements. Embodiments disclosed herein seek to ameliorate these disadvantages and provide more robust measurements of dynamic scattering objects for medical and industrial applications.

SUMMARY

The disclosure describes novel methods, devices, and systems for collecting and evaluating the interference pattern, or speckle pattern, produced by the scattering of coherent or partially coherent light to determine the rate of movement of the scattering particles. In a particular non-limiting case, the disclosed methods, devices, and systems may be used in a clinical setting to determine the flow rate of blood cells within vascularized tissue. In a second non-limiting case, the disclosed methods, devices, and systems may be used for determining particle size in a solution of light scattering particles. In a third case, the disclosed methods, devices, and systems may be used to determine heart rate, by evaluating the periodicity of blood flow during the cardiac cycle.

The embodiments disclosed herein rely on the innovative concept of replacing the conventional camera and laser source of LSI, which illuminates and records images at a distance, with a sensor and laser source affixed to a structure (e.g. a housing structure), and with a known separation that substantially reduces back-reflected light waves from the surface (i.e. specularly or diffusely reflected light) from entering the detection field. Some embodiments also disclose affixing of the structure to the sample of interest, so that the sample cannot move independently of the light source and detector. Some embodiments also discloses a transfer of data to a processing algorithm, wherein a metric of image contrast is calculated in space and/or in time. In a non-limiting case, the light source may be a vertical-cavity surface-emitting laser (VCSEL), the sensor may be a complementary metal-oxide-semiconductor (CMOS) image sensor, and the structure may be a wearable band, which affixes to a person's wrist or other extremity.

The disclosed embodiments may include any structure adjoining the light source and detector designed to eliminate photons exiting an area of illumination on the sample surface from entering the detector. The area of illumination can be defined as the intersection of the cone of light delineated by the full-width-half-maximum intensity of the emitted light with the sample surface. In traditional imaging setups, a light source will intentionally be aimed to illuminate the surface that is imaged by a camera. The disclosed embodiments specifically avoid imaging any area illuminated by the light source. The purpose of blocking detection of photons emitted from the area of illumination is that these photons are more likely to have undergone specular or diffuse reflection off the sample surface. The present technique prefers photons that have penetrated deeply and multiply-scattered within the sample, to increase the probability of light scattering interactions with flowing/moving particles.

In some embodiments, a system for determining the rate of movement of a plurality of light scattering particles within a sample is disclosed. The system includes a light source, a photo-sensitive detector, a structure adjoining the light source and the detector for operatively positioning the light source and the detector adjacent the sample, and a processor. The light source is configured to emit at least partially coherent light toward the plurality of light scattering particles. The detector has one or more pixels and is configured to detect light scattered off of at least some of the plurality of light scattering particles. The structure is configured to position the light source and the detector relative to one another and the sample such that surface reflections from the sample are not detected by the detector and such that at least some of the emitted light scattered off of at least some of the plurality of light scattering particles is detected by the detector. The processor is operably coupled to the detector and is programmed to derive a metric of contrast by comparing in time and/or space the light detected by the one or more pixels. The processor is further programmed to relate the metric of contrast to the rate of movement of the light scattering particles within the sample. The processor may be physically adjoined to the structure or may not be physically adjoined to the structure. The processor may be configured to wirelessly receive data from the detector.

The light source and the detector may be positioned approximately the same normal distance (h) from a surface of the sample, wherein the at least partially coherent light is emitted from the light source with a known angle of projection ($\theta$) along an optical emission axis substantially normal to the surface of the sample. The light source and detector may be spaced apart along the same surface by a distance greater than $2h \tan(\theta/2)$. The structure may be configured to maintain the light source, the detector, and the sample in a constant spatial relationship during detection.

The metric of contrast may be a standard deviation from the mean, a median, a percent difference, a potential-well fill time difference, a gradient between pixels, and subtraction between pixels or subregions of pixels. The plurality of light scattering particles may include blood cells. The system may be configured to measure blood flow. The processor can be further programmed to determine blood circulation adequacy based on the measured blood flow.

The structure may include a housing containing the light source and the detector. The housing may contain the processor. The structure may be in the form of a patch configured to be applied to a skin surface of a user. The structure may include an adhesive material for affixing the structure to a surface of the sample. The structure may be configured to be coupled to the sample by means of friction. The structure can include a securing mechanism to secure the structure adjacent to a surface of the sample during detection. The securing mechanism may be, for example, a spring loaded clip, a belt, or a strap. The structure may be configured to be affixed to a region of skin of a user. The structure may be configured to be worn by a user. The structure can be in the form of a wrist band.

The system may be configured to measure the rate of movement at a depth into the sample between about 1 mm and about 1 cm. The detector may be selectively spaced from the light source a separation distance that allows the detector to target light scattered from a selected depth into the sample for interrogation. The separation distance between the light source and the detector may be adjustable. The detector may be a CMOS or CCD sensor. The light source may be a laser. The light emitted by the light source may be within the near-infrared spectrum. The light emitted by the light source may be between about 700 nm and about 900 nm. The system can configured to place the structure in substantially direct contact with a surface of the sample. The system may include a display for displaying an image of a detected speckle pattern or a numerical or graphical representation of a speckle contrast, rate of movement, depth of penetration, or another measure derived therefrom. The display may be adjoined to the structure. The detector may be configured to accept unfocused light rays. The detector can be configured to accept light paths that have not been altered by optical elements which modify the path or direction of impinging light, including lenses.

The structure can include an opaque divider which is configured to limit a numerical aperture of the light source and/or the detector such that the numerical apertures of the light source and detector do not overlap on a surface of the sample. The opaque divider can be an opaque sheet or block positioned between the light source and the detector. The opaque divider can be an opaque housing positioned operatively in front of the detector. The opaque housing can include an aperture for limiting the angle of detection by the detector.

The structure may be rigid along a portion between the light source and the detector. The one or more pixels of the detector may have a detection area having a center, wherein the structure is configured such that an axis of peak emission of the light source is not substantially directed at or substantially aligned with the center of the detection area. The structure can be configured such that the axis of peak emission is not substantially directed at or substantially aligned with any part of the detection area.

In some embodiments, a method for determining the rate of movement of a plurality of light scattering particles within a sample is disclosed. The method includes positioning a structure adjacent a surface of the sample. The structure adjoins a light source configured to emit at least partially coherent light and a photo-sensitive detector having one or more light-sensitive pixels. The positioning places the light source at a first site adjacent the sample. The structure is configured to orient the light source at the first site relative to the sample such that at least part of the sample is within the emission numerical aperture of the light source. A cone of light emitted by the light source and defined by the full-width-half-maximum divergent intensity of the emitted light defines an area of illumination on the surface of the sample. The positioning further places the detector at a second site adjacent the sample. The structure is further configured to orient the detector at the second site relative to the sample such that at least part of the sample is within the acceptance numerical aperture of the detector and such that light directed from or through the area of illumination is prohibited from entering the detector and reaching the light-sensitive pixels. The method further includes actuating the light source, such that light is directed toward the light-scattering particles, and using the detector to detect light emitted from the light source and scattered by at least some of the light-scattering particles. The method further includes transferring signals related to the detected light from the detector to a processor; comparing in time and/or space the light detected by the one or more pixels; deriving a metric of contrast based on the comparison; and relating the metric of contrast to the rate of movement of the light scattering particles.

Positioning the structure may include coupling the structure to the sample. The structure may be coupled to the sample by an adhesive material. Coupling the structure may include applying a patch to the skin of a user. The structure may be frictionally coupled to the sample. Frictionally coupling the structure may include applying a strap, belt, or spring-loaded clip to the sample. The structure may be rigid along a portion between the light source and the detector. The structure can be configured to be worn by a user. The method may further include adjusting a separation distance along the structure between the light source and the detector. The structure may be in the form of a wrist band. The structure may coupled adjacent to the skin of a user. The detector can be a CMOS or CCD sensor. The light source can be a laser. The light emitted by the light source may be within the near-infrared spectrum. The light emitted by the light source may be between about 700 nm and about 900 nm. Positioning the structure may include placing the structure in substantially direct contact with the surface of the sample. Positioning the structure can include placing the light source in substantially direct contact with a surface of the sample and placing the detector in substantially direct contact with the surface of the sample. The method may further include displaying an image of a detected speckle pattern or a numerical or graphical representation of a speckle contrast, rate of movement, depth of penetration, or another measure derived therefrom.

The detector may be configured to accept unfocused light rays. The detector may be configured to accept light paths that have not been altered by optical elements which modify the path or direction of impinging light, including lenses. The method may further include positioning an opaque divider before, after, or simultaneously with the positioning of the detector. The opaque divider can be configured to limit the numerical aperture of the light source and/or the detector such that the numerical apertures of the light source and the detector do not overlap one another on a surface of the sample. The opaque divider can be an opaque sheet or block positioned at a third site between the first site and the second site. The opaque divider can be an opaque housing positioned operatively in front of the detector. The opaque housing can include an aperture for limiting the angle of detection by the detector.

The method may further include selecting a depth within the sample for targeting interrogation of scattered light and determining a separation distance between the light source and the detector configured to target the selected depth. The first site and the second site may be separated by the determined separation distance. Using the detector to detect light may include detecting light emitted from the light source and scattered by at least some of the light-scattering particles at a first depth within the sample. The method may further include adjusting a separation distance along the structure between the light source and the detector and using the detector to detect light emitted from the light source and scattered by at least some of the light-scattering particles at a second depth within the sample. Transferring signals can include wirelessly transferring signals.

The light source and the detector may be positioned approximately the same normal distance (h) from a surface of the sample, wherein the at least partially coherent light is emitted from the light source with a known angle of projection ($\theta$) along an optical emission axis substantially normal to the surface of the sample. The light source and detector can be spaced apart along the same surface by a separation distance greater than $2h \tan(\theta/2)$.

The light scattering particles can include blood cells. The method can include relating the rate of movement of light scattering particles to blood flow. The method can further include determining blood circulation adequacy based on the measured blood flow. The method can further include maintaining the light source, the detector, and the sample in a constant spatial relationship during detection. The metric of contrast may be a standard deviation from the mean, a median, a percent difference, a potential-well fill time difference, a gradient between pixels, or subtraction between pixels or subregions of pixels.

Using the detector to detect light can include detecting light emitted from the light source and scattered by at least some of the light-scattering particles at a depth within the sample between about 1 mm and 1 cm. The one or more pixels of the detector can have a detection area having a center, wherein the structure is configured such that an axis of peak emission of the light source is not substantially directed at or substantially aligned with the center of the detection area. The structure can be configured such that the axis of peak emission is not substantially directed at or substantially aligned with any part of the detection area.

BRIEF DESCRIPTION OF THE DRAWINGS

The embodiments disclosed herein are intended to be within the scope of the invention herein disclosed. These and other embodiments will be apparent from the following detailed description having reference to the attached figures, the invention not being limited to any particular disclosed embodiment(s). Optional and/or preferred features described with reference to some embodiments may be combined with and incorporated into other embodiments.

FIGS. 1A-1D illustrate a comparison of the fields of emission and detection in a conventional laser speckle imaging system (FIG. 1A) with a housed laser speckle imaging system (FIG. 1B).

DETAILED DESCRIPTION

Disclosed herein are novel methods, devices, and systems for determining a more accurate rate of movement (e.g., flow rate, diffusion rate, etc.) of scattering particles within a sample of interest. Broadly, the disclosed embodiments innovatively apply the theory of dynamic light scattering, and in particular a speckle contrast analysis method. The method of speckle contrast imaging is commonly used to image blood vessels and other vascularized tissues within the field of biomedical engineering. The method takes advantage of the interference pattern formed when coherent laser light scatters randomly in a sample media. The so-called speckle pattern is formed onto an image sensor. If the scattering objects are in motion, the speckle pattern will fluctuate during the exposure time of the image sensor, which will cause a blurring of the pattern. For a given camera exposure, faster fluctuations induce more blurring. One measure of the "blur" in a speckle image is commonly referred to as the speckle contrast, and is conventionally defined as:

$$K = \sigma / \langle I \rangle \quad [1]$$

where $\sigma$ is the standard deviation and $\langle I \rangle$ is the mean of N pixel intensities (for a silicon image sensor, the pixel intensity is proportional to the voltage output from the detector element). As a non-limiting example of relating a metric of contrast to the flow rate of moving particles, the spatial speckle contrast can be related to the autocorrelation time of the speckle image, which can then be related to the mean square displacement (e.g., flow speed or diffusion) of the moving scattering objects. In general, a relatively high contrast speckle pattern will produce higher values of K and a more blurry pattern will produce lower values of K. The flow within a sample can then be related to the contrast, which can be computed either through analytic or empirical means. The rate of movement may be determinable through calibration of a given system in a particular configuration with samples of known rates. In some embodiments, the rate of movement may be determined as the velocity, or average velocity (e.g., m/s), of the moving light scatterers within a sample. The flow rate may be a measure of the volume of fluid (e.g., blood) transported per unit of time (i.e. volumetric flow) and may be represented in any suitable units (e.g., $m^3/s$). In some embodiments, the flow rate may be determined as a measure of volumetric flux (e.g., $m^3 \cdot s^{-1} \cdot m^{-2}$) through, for example, a blood vessel or blood vessels.

The disclosed methods, devices, and systems relate to performing improved speckle contrast measurements, which improves the accuracy, reliability, and depth penetration within a sample of interest. The systems, devices, and methods disclosed herein may incorporate component devices, including a light source 100, a detector 200 (i.e. a photosensitive detector, such as an image sensor), and one or more processors, which may be operatively connected to one another to interrogate a sample. In many embodiments, the sample may be a physiological sample, such as a region of tissue on a subject, about which physiological information is to be ascertained. The subject may be a living animal, such as a human. The component devices may be standard devices employed in new configurations, methodologies, and/or systems or they may be devices specifically designed or adapted to perform in the systems and methods disclosed herein. The light source 100 may be configured to emit at least partially coherent light. The light source 100 may be a laser, such as a diode laser. In some embodiments, the light source 100 is a VCSEL laser. The detector 200 may comprise one or more light-sensitive elements (e.g., pixels) for detecting light recovered from the light source 100 after interaction with a sample. The detector 200 may, for example, be a silicon camera sensor. The camera sensor may be of any suitable type, including but not limited to CMOS or CCD image sensors. The detector 200 may comprise or be coupled to an optical element 202, for example a lens. The optical element 202 may include a slit, aperture, or other element for modulating the angle of light (i.e. the amount of light) detected, as described below. In some embodiments, the detector 200 may be configured without any optical elements 202 and/or may be configured to accept unfocused light as described below. The detector 200 may be configured to generate one or more signals related to the detected light and to transmit these signals to the processor. The signals may comprise quantifiable information about the intensity of light detected at one or more pixels at a point in time or over a course of time. In some embodiments, the signals may comprise information about the wavelength(s) of the detected light. The signals may be analog or digital. If the signals are analog they may be subsequently converted into digital signals either before or after being transmitted from the detector 200.

Advantageously, the images detected by the detector 200 of the present disclosure can be unfocused. The rate of motion (e.g., flow rate) can be determined from a global average of the detected speckle contrast rather than by mapping the detected speckle pattern to focused light scattering particles. Configuring the detector 200 to obtain focused images can be expensive and spatially constraining. Detectors 200 configured to accept unfocused light may advantageously be smaller and may be more suitable to be worn by a user. As such, the detector 200 may be configured to accept unfocused (i.e. non-convergent) light rays. For example, the detector 200 may be configured to accept raw unaltered light paths that have not been altered by optical elements, such as a lens, which modify the path or direction of the impinging light.

The disclosed methods, systems, and devices may be particularly useful for LSI systems configured in reflection geometries, as opposed to transmission geometries. In reflection geometries, the light source 100 and the detector 200 are positioned adjacent a same side of the sample, while in transmission geometries they are positioned on opposite sides of a sample. Generally, detectors 200 positioned in transmission geometries could detect at least a portion of any light that is transmitted through the sample without scattering. Detectors 200 positioned in reflection geometries can only detect light emitted from the light source 100 that is reflected and/or scattered by the sample. Reflection geometries may be more suitable for large samples (e.g. certain regions of the body) in which it is impracticable to position a detector 200 on the opposite side of the sample, for example, because the emitted light would be too diffuse or largely absorbed to have any significant informational value. For samples with less well-defined geometries or with less well-defined sides (e.g. an arm), a detector 200 may be considered to be positioned on the same side of the sample if it is in a reflection geometry (i.e. theoretically incapable of detecting any non-scattered transmitted light from the light source 100). In some instances, the detector 200 may be positioned within the broad distribution of emitted light defined by, for example, the Gaussian profile of the laser light emitted from the light source 100, but may be positioned outside of a narrower measure of the emitted light beam, such as the full-width-half-maximum divergent intensity cone of light emitted by the light source 100.

Figure 1A:
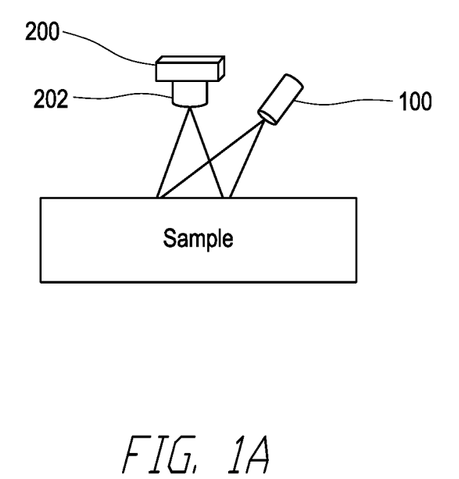
FIG. 1A schematically illustrates an example of a conventional system.
Figure 1B:
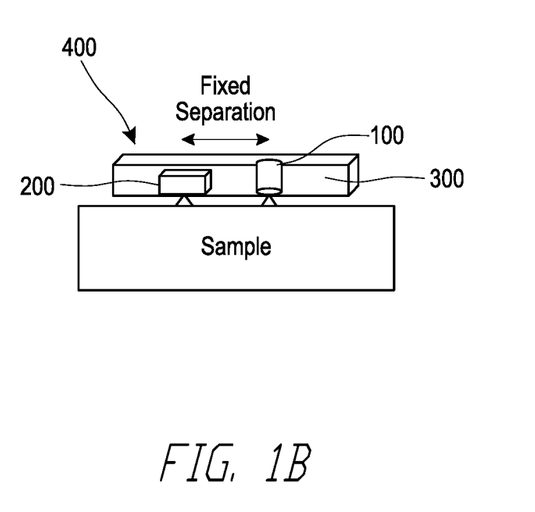
FIG. 1B schematically illustrates an example of a housed system.
Figure 1C:
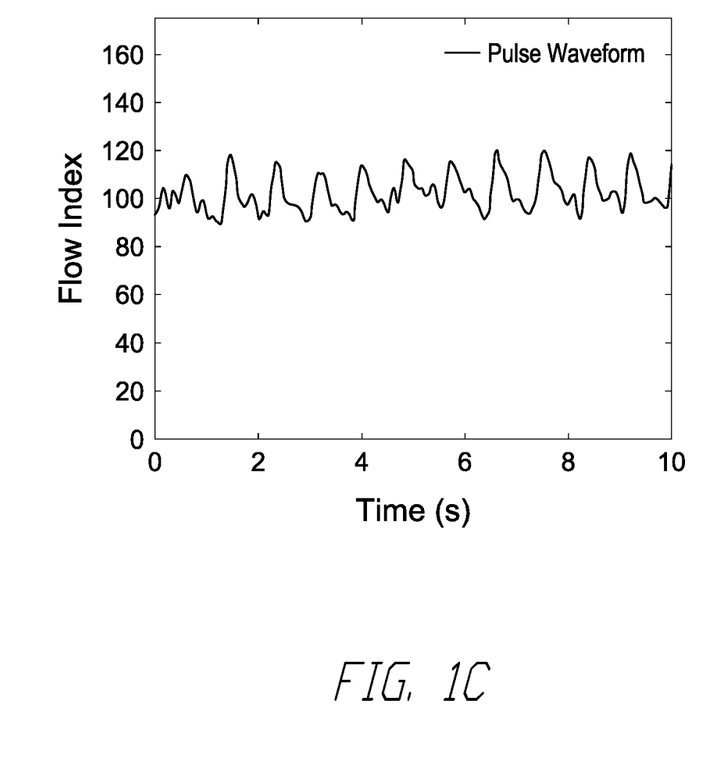
FIG. 1C depicts an example of flow index data generated using a conventional system to measure pulsatile blood flow.
Figure 1D:
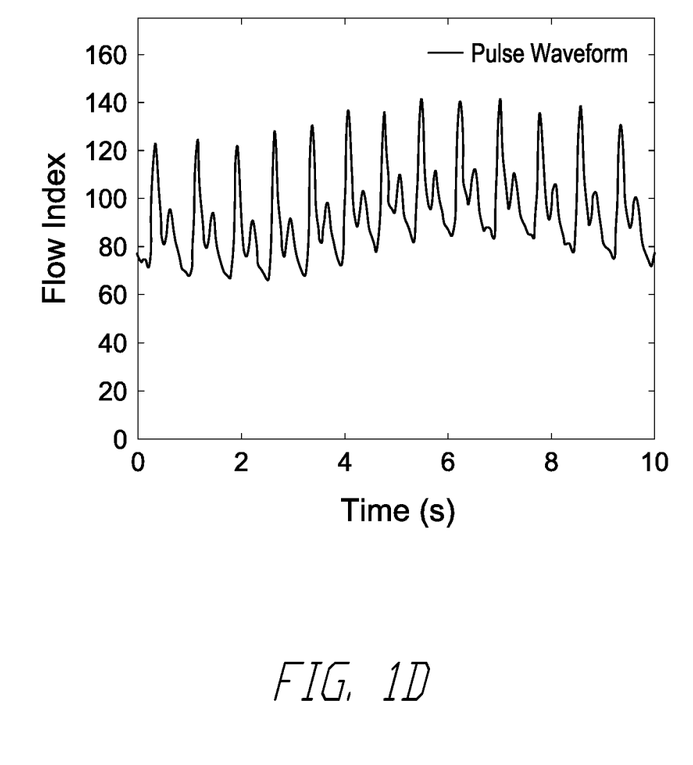
FIG. 1D depicts an example of flow index data generated using a housed system to measure pulsatile blood flow.

The disclosed system can include a structure 300 that adjoins (e.g., houses) both the light source 100 and detector 200 in a fixed (possibly adjustable) orientation, the orientation including a predetermined separation distance. The light source 100, detector 200, and structure 300 can comprise a device 400 for improved interrogation of samples. In many embodiments, the device 400 is configured to be coupled to sample for providing improved interrogation. Other components of the system can be integrated into the device 400 as well (e.g., adjoined to the structure 300), including but not limited to processors, circuits, memory, displays, securing mechanisms, etc. FIGS. 1A-1D compare a conventional LSI system (FIGS. 1A and 1C) to a housed LSI system (FIGS. 1B and 1D) that positions the light source 100 and detector 200 adjacent to the sample and at a fixed separation distance from each other, as described herein. The light source 100 has a numerical aperture which characterizes the range of angles over which the light source 100 emits light (i.e. the solid angle of projection), while the detector 200 has a numerical aperture which characterizes the range of angles over which the detector 200 can accept light (i.e. the angle at which a photon can enter the detector 200 or the solid angle of detection). As shown in FIG. 1A, the numerical apertures of the light source 100 and the detector 200 overlap on the sample surface in a conventional LSI system so that the imaged surface is directly illuminated (i.e. the detector 200 images at least a portion of the area of illumination). However, as shown in FIG. 1B, the structure 300 configures the light source 100 and the detector 200 of the housed system such that the numerical apertures do not overlap on the surface of the sample and a part of the sample outside of the imaging field is illuminated (i.e. the light source 100 is configured to illuminate an area of illumination outside of the imaging field of the detector 200). FIGS. 1C and 1D depict data collected from non-invasive interrogation of vascularized tissue using LSI. The measured waveforms correlate to the pulsatile blood flow originating from the cardiac cycle. The pulsatility reflects the changes in the volumetric flow rate as the subject's heart pumps blood through the interrogated vasculature. FIG. 1C depicts an example of flow index data generated using a conventional LSI system to interrogate blood flow, in which reflected light and scattered light are both detected by the detector 200. FIG. 1D depicts an example of flow index data generated using a housed system in which the light source 100 and detector 200 are configured to exclude reflected light from the detector 200. The more well-defined signal depicted in FIG. 1D is dominated by multiply scattered light from within the sample, as will be described herein, which produces a more pulsatile signal with higher informational content relating to the flow of light scattering particles (e.g., blood cells).

The structure 300 provides a means to orient the numerical aperture of the light source 100 and detector 200 to a desired configuration, and to maintain a fixed configuration during detection. In some embodiments, the structure 300 is able to be coupled to the sample so that the configuration may be maintained relative to the sample, even if the sample is in motion during detection. When maintained in a constant spatial orientation, the light source 100, detector 200, and sample remain separated by substantially the same distances and the direction or axis of emission or detection of the light source 100 and the detector 200 remain oriented at substantially the same angles relative to the sample and relative to each other.

The structure 300 can include any structure that establishes a light source 100 and detector 200 configuration that eliminates or prohibits specularly or diffusely reflected photons (i.e. surface reflections) from entering the detection field of the detector 200. Specular reflectance refers to mirror-like reflection, often occurring on smooth surfaces, where the incident angle is equal to the reflection angle to the surface normal. Diffuse reflectance refers to randomly-oriented surface reflection occurring on rough surfaces (such as matte paint or paper). Photons that undergo diffuse reflectance scatter from the sample surface in a random direction but do not penetrate into the sample. Specular and diffuse reflections contain no informational content about the moving light scattering particles within the sample, and, therefore, it is desirable to avoid detecting this light so as not to dilute the informational content of the detected light. The structure 300 which adjoins and spatially orients the light source 100 and the detector 200 relative to each other and relative to the sample can be used to effectively prohibit the detection of specular reflections by the detector 200.

Figure 2A:
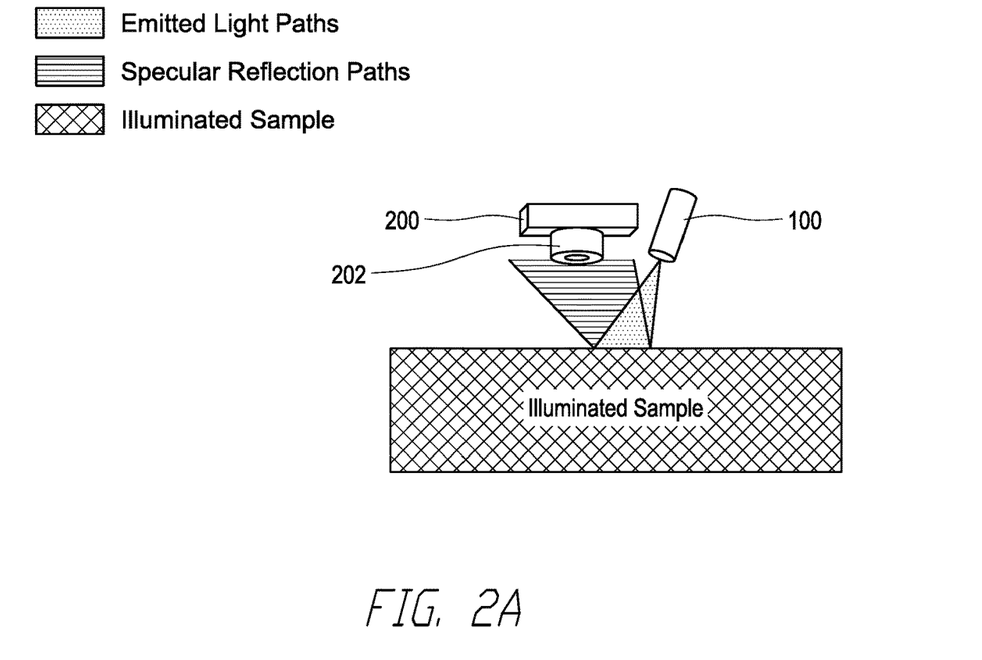
FIGS. 2A-2B illustrate a comparison of the spatial configuration of the components and sample in a conventional laser speckle imaging system (FIG. 2A) with a housed laser speckle imaging system (FIG. 2B) and the ability of the systems to detect surface reflected light.
Figure 2B:
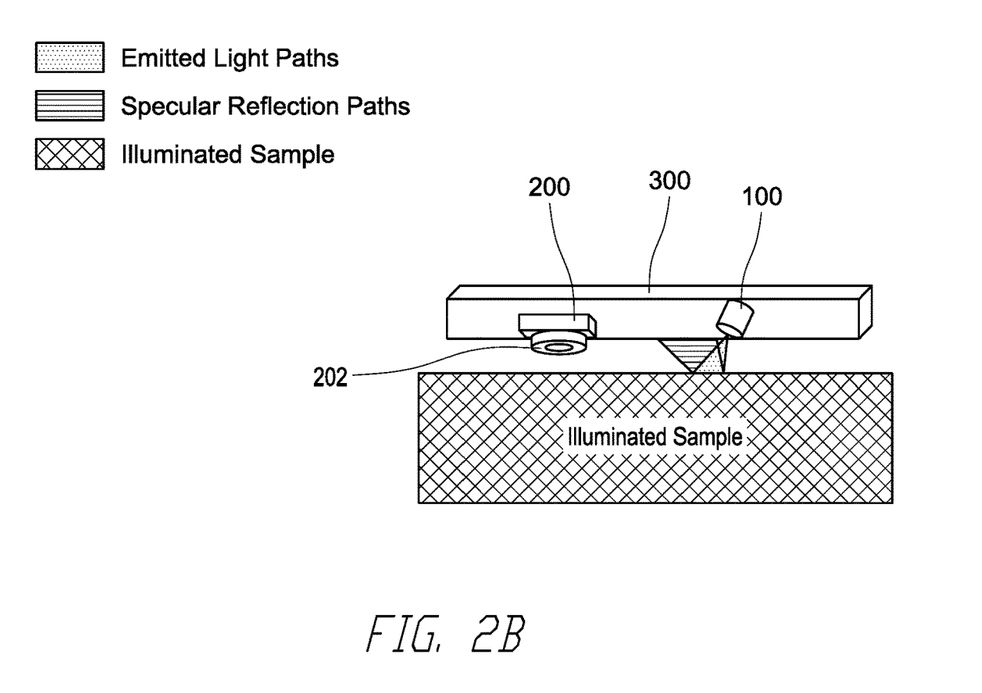

In some embodiments, such a configuration that eliminates or prohibits detection of specular and/or diffuse reflections may be accomplished, at least partially, through controlling the proximity of the light source 100 and/or detector 200 to the sample surface, which can be effectively controlled by the positioning of the structure 300 relative to the sample surface, as shown in FIG. 2B. FIGS. 2A and 2B compare a conventional LSI system (FIG. 2A) to a housed system (FIG. 2B), in which the light source 100 and detector 200 of the housed system are positioned closer to the surface of the sample than in the conventional system. The light source 100 and detector 200 in FIG. 2A are positioned close enough together and far enough from the surface of the sample, such that back-reflected light, including specular reflections (shown) and diffuse reflections (not shown), of the emitted light from the light source 100 are able to enter the detector 200 (i.e. the reflected light from the emission cone of the light source 100 is within the numerical aperture or detection field of the detector 200). In contrast, the light source 100 and detector 200 in FIG. 2B are positioned with a sufficient separation distance from each other and in close enough proximity to the surface of the sample so that the specular reflections (shown) and diffuse reflections (not shown) of the emitted light from the light source 100 do not reach the detector 200 (i.e. the reflections are not within the numerical aperture of the detector 200 and are physically prohibited from entering the detector 200). Because the detector 200 can include a slit or aperture (e.g., in optical element 202) that confines the angle of detection, the positioning of the detector 200 can be configured to exclude even diffusely reflected light that is able to reach the detector 200 structure from outside the angle of detection. The reflections may diverge at an angle as they propagate from the surface of the sample. The structure 300 can place the detector 200 out of the range of the reflected light by positioning the detector 200 closer to the surface of the sample (if the detector 200 is not positioned over the area of illumination) and/or further away from the light source 100. A detector 200 that is positioned closer to the surface of the sample may need not be positioned as far from the light source 100 as a detector 200 that is positioned further from the surface of the sample, in order to avoid detecting reflected light and vice-versa.

The structures 300 disclosed herein may be configured to space the light source 100 and detector 200 a fixed distance from each other and/or position the light source 100 and the detector 200 a fixed distance away from the surface of the sample when the structure 300 is coupled to the sample. For example, the structure 300 may include means for affixing, coupling, and/or securing the light source 100 and the detector 200 to the sample, such that each is positioned approximately a set distance from the sample surface. For instance, the structure 300 may comprise a wearable device 400, such as a wrist band (e.g., a wrist watch), which positions the light source 100 and the detector 200 substantially adjacent to the skin of a user. The structure 300 may be configured to be in substantially direct contact with a surface of the sample when coupled or may be configured to be set back a distance from the surface of the sample when coupled. When the structure 300 is positioned in substantially direct contact with the sample, it may position the light source 100 and/or the detector 200 in substantially direct contact as well, depending on their orientation relative to the structure 300.

Figure 3:
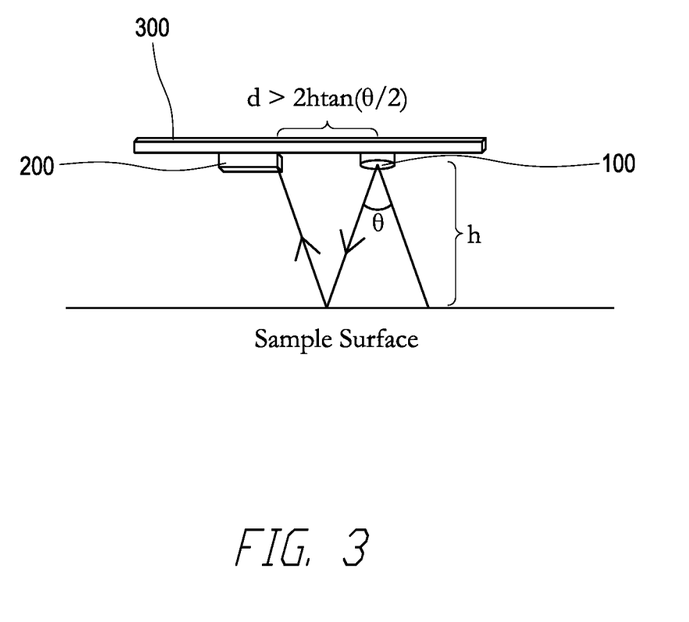
FIG. 3 illustrates the geometry of an LSI system for calculating the minimum source-detector separation distance that must be configured to forbid specular reflections from entering the detector.

In the case where the optical emission axis of the light source 100 is normal to the sample surface, as illustrated in FIG. 3, the light source 100 being positioned a distance h from the sample surface and with divergence angle θ, the closest point of the detector 200 must be separated from the emission point by an amount exceeding $$d > 2\,h\,\tan(\theta/2) \quad [2]$$

in order to prohibit specular reflections from entering the detector 200, positioned the same distance h from the sample. As schematically depicted in FIG. 3, the outermost specularly reflected photon will bounce off the sample surface at the divergence angle θ relative to the incident path of emitted light. At a normal distance h from the surface of the sample, this photon will be a distance equivalent to $2h\,\tan(\theta/2)$ from the emission point of the emitted light. Therefore, the closest point of the detector 200 that can accept photons (at any angle or at the angle of the outermost specularly reflected photon) must be separated from the emission point of the light source 100 by a minimum distance greater than $2h\,\tan(\theta/2)$ to avoid detection of specular reflections. This value can provide a useful guiding parameter for configuring the adjoining structure 300 to position the light source 100 and detector 200 an appropriate separation distance from each other along the surface of the sample. Appropriate separation distances for other orientations of the light source 100 and detector 200 (e.g., positioned off the normal or at different distances from the surface) can be similarly calculated, either analytically or empirically.

Increasing the distance between the detector 200 and light source 100 can confer other advantages to the LSI system as well. For example, it has been shown through Monte Carlo simulations of the radiative transport equation that the average number of scattering events and the depth of penetration of a photon emitted by a light source and detected by a detector positioned in a reflection geometry increases with increasing separation distance between the light source 100 and detector 200. In other words, the further apart the light source 100 and detector 200 are separated, the more likely the detector 200 is to capture photons that have penetrated further into the sample and that have scattered multiple times within the sample. Increasing the occurrence of multiple scattering and the depth penetration within the dynamic regions of the sample can give more accurate and robust signals, which may contain higher contents of relevant information. For instance, increasing the number of scattering events increases the probability that a photon will scatter off of a moving light scattering particle (rather than simply a static light scattering particle), increasing the relevant informational content of the detected scattered light. Thus, the disclosed methods, systems, and devices can be used to create a selection bias of photons that have multiply scattered within the sample. Increasing the depth of penetration, such as in a sample of vascularized tissue, can, for example, better target blood vessels beyond the epidermis (e.g., more than 0.5 mm into the tissue). Based on these calculations, the separation distance between the light source 100 and the detector 200 as configured by the adjoining structure 300, can be used to target specific depths of penetration within the sample. The light source 100 and detector 200 may be configured with a larger separation distance to target deeper regions of the sample and vice-versa. In some applications, such as the determination of blood flow, the structure 300 may be configured to target and accurately resolve blood flow at depths between 0.1 mm and 1 cm within the tissue sample.

In some embodiments, the structure 300 may be configured such that the separation distance between the light source 100 and the detector 200 is adjustable. For example, the light source 100 and detector 200 could be movably positioned along a linear axis. The light source 100 and the detector 200 could be brought closer together or further apart either by moving one or the other or by moving both. Any suitable mechanical means could be used to translocate the light source 100 and/or the detector 200. For example, they could be slidably coupled to a rail. In another example, the structure 300 may comprise one or more threaded connections between two sides of the structure 300 which can be screwed closer together or further apart. The separation distance may be tuned by turning of a screw or a wheel. The moveable elements may include locking mechanisms for temporarily locking in a position or they may be frictionally held in place absent an intentional adjustment force. In some embodiments of the disclosed method, the sample may be interrogated at multiple depths of penetration and/or the depth of penetration may be adjusted until a desirable signal is detected. The processor may be configured to estimate an interrogation depth based on the separation distance, which could be based on a prior calibration.

Figure 4:
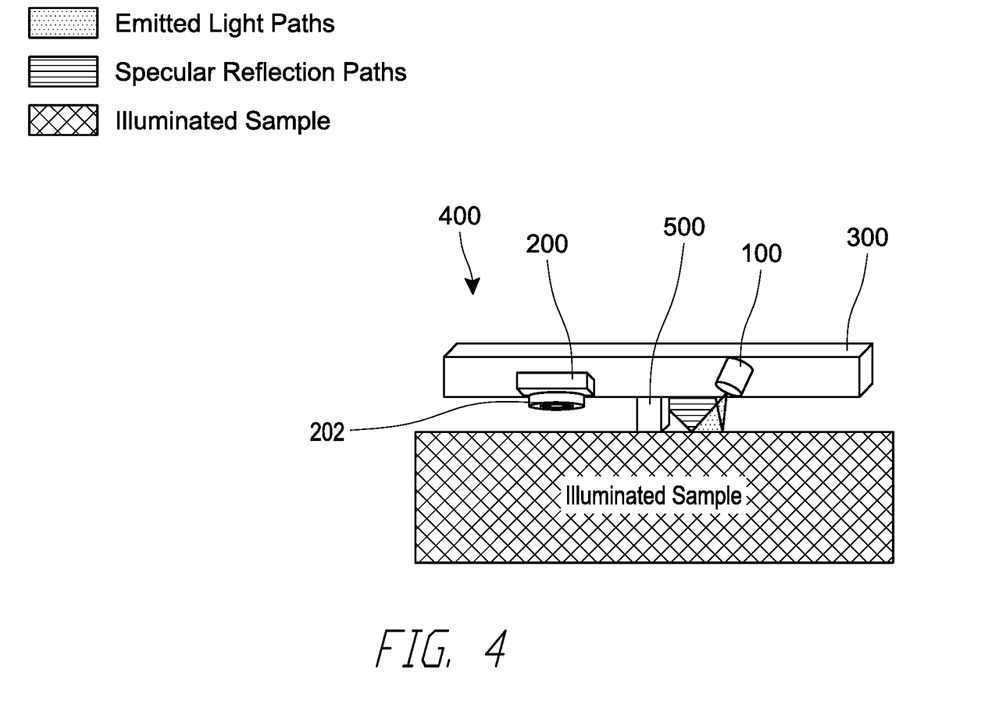
FIG. 4 illustrates an example of a device configuration in which the structure is coupled to an opaque divider which contacts the sample and serves to prevent light reflected from the surface of the sample from reaching the image sensor of the detector.

Additional configurations may also be used to prohibit specular and diffuse reflection, such as the placement of an opaque divider 500 (e.g., an opaque sheet or block) between the detection and emission element (i.e. detector 200 and light source 100) that blocks reflected photons from entering the detector 200. In such configurations, the light source 100 and detector 200 may be placed close enough to each other such that the numerical apertures of the light source 100 and detector 200 would normally overlap on the surface of the sample (i.e. the detector 200 would image the area of illumination), but is prevented from doing so by the opaque divider 500, which can be used to block incident rays of emitted light and/or specularly or diffusely reflected light from passing through the opaque divider 500. FIG. 4 illustrates the use of an opaque divider 500, which blocks the reflected light from reaching the detector 200. The opaque divider 500 can be adjoined to the same structure 300 as the light source 100 and the detector 200. It can be configured to be detachable/replaceable and/or selectively positionable between the light source 100 and the detector 200. It may have a height that extends substantially to the surface of the sample, as shown in FIG. 4, or may be a lesser height. In some embodiments, the structure 300 may be configured to couple to various different dividers 500 of different configurations and/or may be configured to accept or receive multiple dividers 500.

Figure 5:
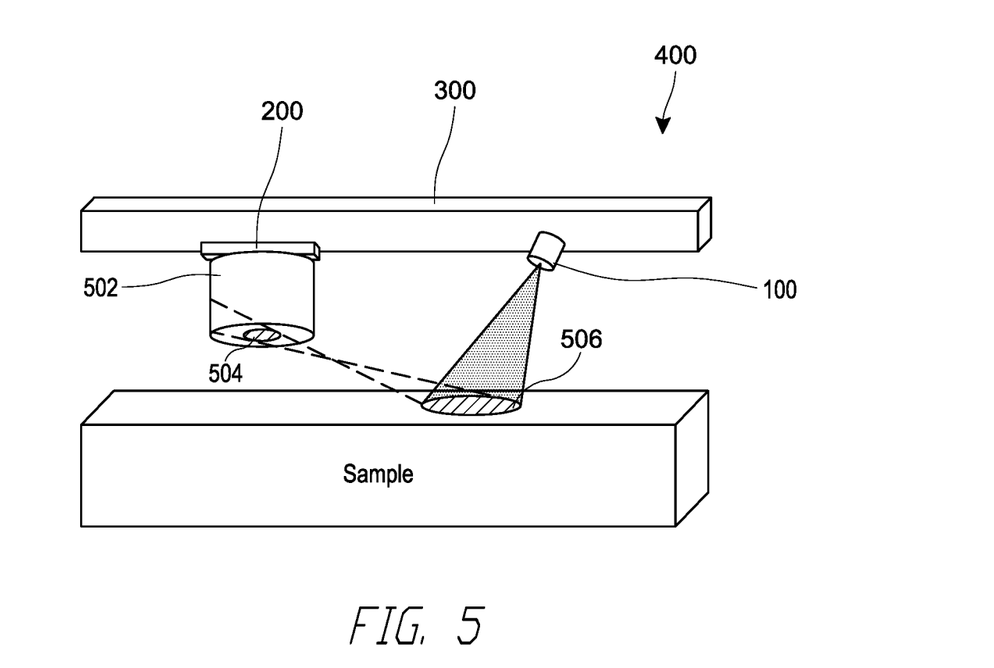
FIG. 5 illustrates an example a device configuration that includes an opaque housing with a limiting aperture coupled to the detector.

In some embodiments, an opaque housing divider 502 may place an aperture 504 in front of the detector 200, as described elsewhere herein or similar as to described elsewhere herein, where the acceptance angle of the aperture 504 prevents light from the area of illumination 506 from entering the detector 200. FIG. 5 illustrates an example of an aperture 504 formed within an opaque divider 502 (an opaque housing) and positioned below the detector 200. This configuration prevents photons exiting the area of illumination 506 from entering the detector 200. In this embodiment, photons entering the detector 200 must first pass through the narrow limiting aperture 504 positioned in front of the detector 200 by the opaque housing 502. The aperture 504 serves to geometrically restrict the possible angles of approach from the sample. The aperture 504 is configured to limit the angle of detection by the detector 200 such that no photon reflected form the area of illumination 506, even at maximally steep angles reflected from the edges of the area of illumination as shown, can enter the aperture 504 at an angle that geometrically allows it to reach the detector 200. Any photon ray originating from the area of illumination 506 and passing through the aperture 504 will unable to enter the detector 200. The opaque housing divider 502 may be an external component that is coupled to a standard detector. The opaque housing divider 502 may have different configurations (e.g., dimensions) from standard apertures (e.g., lens apertures) that exist on many standard detectors, in order to prohibit the detection of reflected light from the light source 100.

Analogous to reflective light, significant amounts of ballistic light (i.e. non-scattered and non-reflected light) are also undesirable for detection by the detector 200. In the same way reflected light does not interact with dynamic light scatterers, ballistic photons may pass directly through a translucent sample without scattering at all. Thus, ballistic photons interfere with the accuracy of the measurement, and dilute the informational content of the detected light, reducing the signal-to-noise ratio.

Various embodiments include a structure 300 configuration that controls the angular direction and transverse positioning of the emission profile of the light source 100 relative to the detector 200 and sample. Some embodiments may avoid aiming the bulk of the light source 100 intensity directly at the detector 200, to avoid the over-detection of ballistic photons. Angling the emission profile away from the detector 200 effectively minimizes detected ballistic photons. Generally, laser output beam profiles have a Gaussian shape, with the emission intensity peak in the center of the emitter. Thus, the angle and direction of the axis of peak emission may be configured to avoid direct incidence onto the center of the detection surface (e.g., array of light-sensitive pixels) of the detector 200. In some embodiments, the axis of peak emission may be configured to avoid direct incidence on the detection surface altogether.

Figure 6:
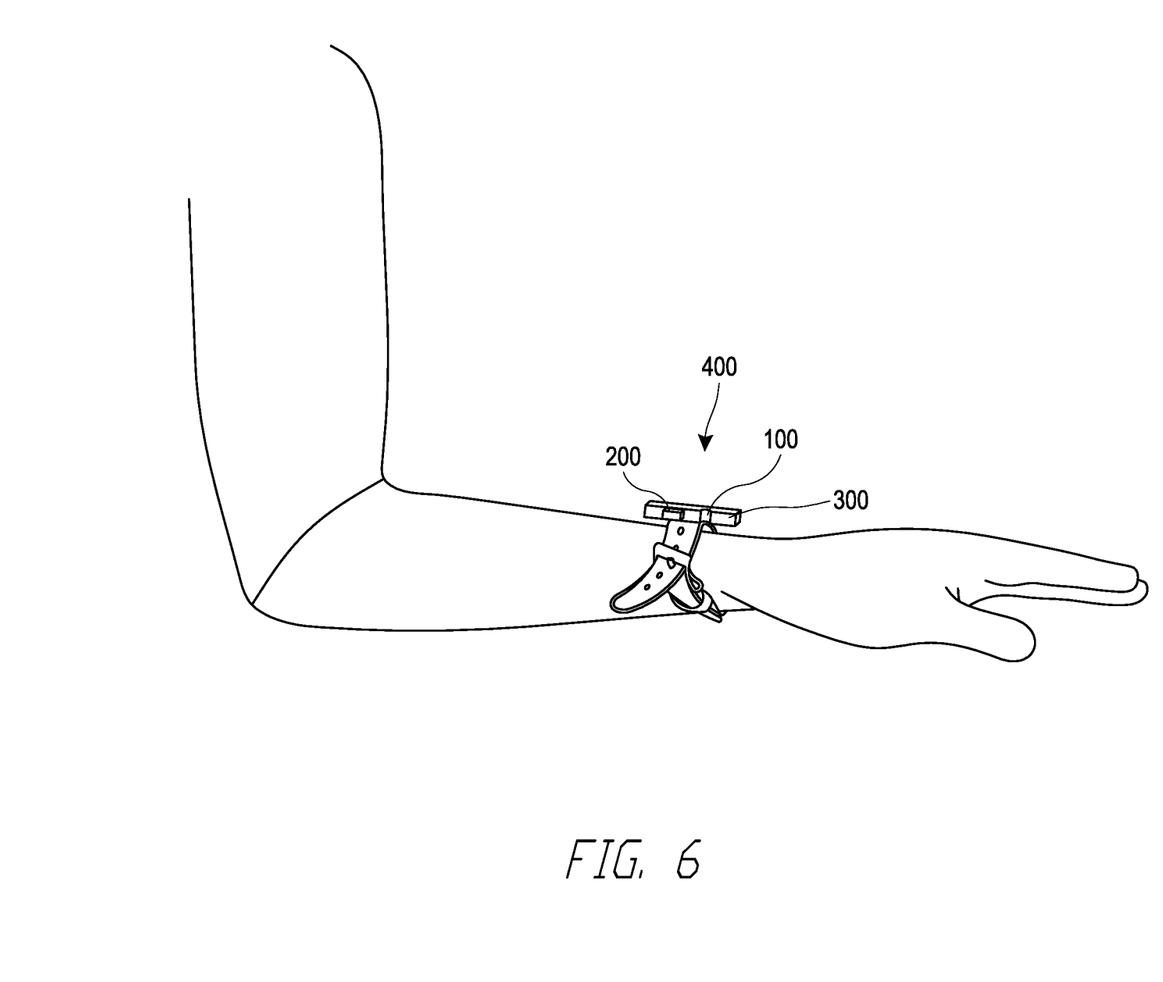
FIG. 6 illustrates an example of one embodiment of the invention, wherein the structure housing the light source and the detector can be fastened to the sample using a wristwatch strap.

Fixing the light source 100 and detector 200 to a structure 300 can ensure that that all three vital elements (light source 100, detector 200, and sample) remain rigidly aligned, even during motion of the sample. This can subsequently reduce motion artifacts and provide consistent illumination intensity. The light source 100 and detector 200 can be permanently/unmovably affixed to the structure. Configuring the light source 100 and detector 100 permanently in a housing allows for consistent depths of interrogation between systems and samples. This concept is illustrated in FIG. 6. FIG. 6 illustrates an embodiment of a device 400 as described herein, which includes a light source 100 (e.g., a diode laser) and a detector 200 (e.g., a CMOS image sensor) affixed to a housing structure 300. The components may be miniaturized relative to conventional LSI components for incorporation into a miniaturized device 400. The housing structure 300 may be substantially rigid, at least where it adjoins the light source 100 and the detector 200, so as to maintain a constant spatial configuration. The housing structure 300 includes or is coupled to a flexible band such that the housing structure takes the form of a wrist band in this particular example. The wrist band can be configured to position the light source 100 and the detector 200 substantially adjacent the skin of the user when it is worn by the user such that the emission numerical aperture of the light source 100 and the detection numerical aperture of the detector 200 are directed toward the skin of the user. The band may be adjustable so that it can position the light source 100 and the detector 200 substantially adjacent the skin of the user regardless of size differences between users. In some instances, the wrist band may be configured to apply tight enough pressure to place the light source 100 and the detector 200 in substantially direct contact with the skin of the user.

The structure 300 adjoining the light source 100 and the detector 200 can comprise other forms suitable for coupling the light source 100 and the detector 200 to a sample and positioning them in an operative configuration (e.g., one that prohibits detection of specular and/or diffuse reflections) relative to a surface of the sample, such as the skin of a user. For example, the structure 300 could be coupled to the sample surface via an adhesive. The adhesive could be applied to the sample and/or the structure 300 prior to operation. In some embodiments, the structure 300 may comprise an adhesive layer configured to affix the structure 300 to the sample surface. The structure may be in the form of a patch (e.g., a relatively flat sheet) with an adhesive layer that affixes to the sample surface (e.g., skin). The light source 100 and detector 200 can be integrated into the patch such that they are spatially configured an appropriate separation distance and such that their numerical apertures are appropriately directed toward the sample. A patch may be especially suitable for a device configured to be coupled to an irregular or curved geometry (e.g., on the torso of a user). In some embodiments, the structure 300 may be coupled to the sample by frictional means of engagement. For example, the structure 300 could include a securing mechanism, such as a spring loaded clip (e.g., to clip to a user's clothing such that the structure 300 is positioned adjacent the skin or to clip to a user's finger), a belt (e.g., for securing the structure adjacent to a user's waist), or a strap (e.g. for securing the structure to an appendage around which the strap is frictionally secured).

The disclosed embodiments also contemplate a transfer of detector 200 data to a processor, and subsequent processing of said data to obtain a contrast metric in space and/or time. Detector 200 signals can be manipulated with advanced digital signal processing circuits, which may, in a non-limiting case, be placed on the same structure 300 as the light source 100 and detector 200. Once converted to digital, signals can be manipulated without degradation of the signal quality. Digital signals can also be conveniently stored into a memory, and/or sent over a wireless electromagnetic carrier band (e.g. Bluetooth). The processor can be part of a single device 400 with the light source 100 and the detector 200 and may be adjoined to the structure 300 (e.g., housing). In other embodiments, the processor may be external to the device 400, although processing circuits may be incorporated into the device 400. Some embodiments may incorporate multiple processors which may be all incorporated into the device 400, all external to the device 400, or distributed between the device 400 and external components. Data may be transferred between the detector 200 and the processor by any suitable means. For example, data can be wirelessly transmitted, transmitted via a wire or cable (e.g., USB cable), downloaded onto a portable memory drive, etc. Once the data has been transferred to a processing element, a contrast metric is calculated. One non limiting example metric of contrast is specified in eq. 1. Other metrics of contrast can be used as well, with contrast being defined generally as any measure of disparity, difference, or distinction between values of multiple pixel elements of the detector, and/or the evolution of a single pixel element over time. Non-limiting examples include statistical properties of the spatial or temporal contrast, such as the speckle flow index (defined as $1/K^2$ where K is the speckle contrast as described herein), standard deviation from mean, median, difference metrics such as mean percent difference (e.g., between pixels of the detector 200), potential-well fill time difference, gradient between pixels, metrics of comparisons between subregions such as subtraction, the magnitude of fluctuation in the pixel intensities over time, reduction of the pixels to local binary patterns or local ternary patterns, etc. An autocorrelation performed on the signal generated by a single pixel over a period of time may quantify the temporal decorrelation in detected light intensity as a result of the motion of the moving light scattering particles.

In some embodiments, the system can include a display, which may be integrated into the device 400 (e.g. coupled along with the light source 100 and the detector 200 to the structure 300) and/or the processor (e.g., part of a general computer, tablet, smart phone, etc. if the processor is external to the device 400) or may be a separate component. The display can be used to display, for example, operating parameters and/or data to a user. In some instances, the display may be used to display an image of the speckle pattern detected by the detector 200 and/or may be used to display a numerical or graphical representation of speckle contrast (e.g., a metric of contrast), the determined rate of movement (e.g., flow rate), the depth of penetration (e.g., a targeted or average depth), any measure derived therefrom, etc. The display may be coupled to an input mechanism (e.g., a keyboard or mouse on a computer or one or more buttons on a device) which may allow a user to toggle between displayed information and/or enter or select input parameters for affecting the calculations. The system may include an interactive software allowing a user to interact with the processor.

The features disclosed above, may produce a more commercially friendly device with applications, including, but not limited to, healthcare and wearable technology. For example, the system could be miniaturized using ultra-compact CMOS sensors and VCSELs. Digital processing circuits could be mounted on the system to perform the specific calculations necessary for determining contrast and/or motion (e.g., flow). The system could then be integrated into a wearable wrist monitor, to perform blood flow monitoring or heart rate monitoring. In another example, the system could be miniaturized and placed on a medical device intended to monitor vascular health. In this example, the medical device could be affixed to tissue of interest to clinicians and the disclosed system and method could be used to measure the flow of red blood cells within this tissue. Specifically, the medical device could, for example, be affixed to a patient's foot so that blood flow could be quantified in this tissue using the disclosed system and method. In such tissue (and others), blood circulation is required to deliver oxygen and remove cellular waste products. As such, a minimal amount of blood flow is required to sustain continued tissue viability such that nutrient delivery is adequate to meet metabolic tissue demands. The disclosed system and method could thus be used to measure blood flow (circulation) in the tissue for the purpose of determining whether the measured quantity is consistent with continued tissue viability, and as such, be used to assess the degree of blood circulation adequacy. The processor may be programmed to compare the measured blood flow (circulation) to a predetermined value and determine whether the blood circulation is adequate.

Working Example

Figure 7A:
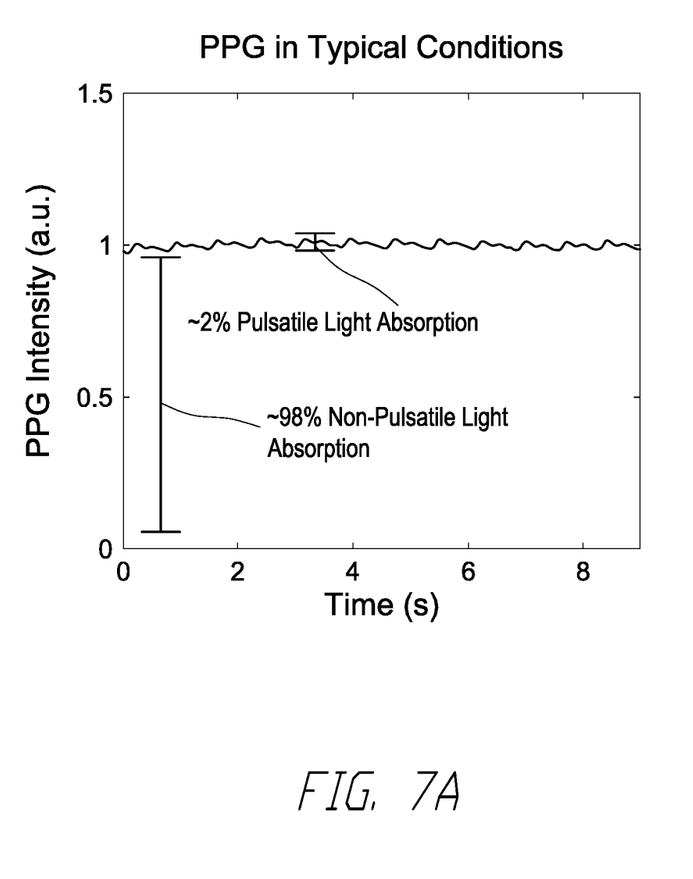
FIGS. 7A-7B illustrate a comparison of interrogation results using standard PPG (FIG. 7A) and LSI according to features disclosed herein (FIG. 7B).
Figure 7B:
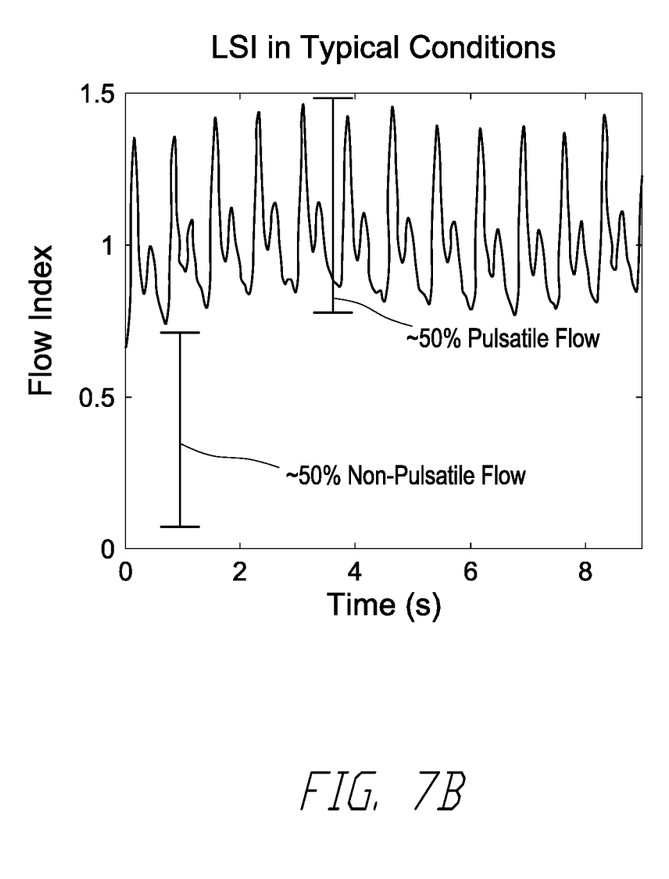

FIGS. 7A and 7B compare the use of photoplethysmography (PPG), the standard technology currently used for optical heart rate monitoring (FIG. 7A), to the use of LSI in accordance with the disclosed methods, systems, and devices (e.g., FIG. 2B) as measured from a housing structure 300 coupled to the wrist for optical heart rate monitoring (FIG. 7B). This example illustrates that flow measurement from the disclosed LSI system is unexpectedly superior to PPG for determining heart rate, because the amplitude of the pulsatile signal is orders of magnitude larger than PPG. For example, as shown in FIG. 7A, the pulsatile signal, arising from change in the absorption of emitted light within the arteries due to the periodic volumetric expansion, comprises about 2% of the signal, while about 98% of the signal is not-pulsatile, arising from absorption of the emitted light by skin, veins, and other tissue. However, as shown in FIG. 7B, approximately 50% of the signal arises from pulsatile flow, while approximately 50% of the signal arises from non-pulsatile flow. The periodicity of the flow arises from the cardiac cycle and can be used to determine heart rate by determining the period between successive waveform features (such as systolic contraction peaks).

While the present invention has been described in terms of particular embodiments and applications, in both summarized and detailed forms, it is not intended that these descriptions in any way limit its scope to any such embodiments and applications, and it will be understood that many substitutions, changes and variations in the described embodiments, applications and details of the method and system illustrated herein and of their operation can be made by those skilled in the art without departing from the spirit of this invention.

What is claimed is:

1. A system for determining a rate of movement of a plurality of light scattering particles within a sample, the system comprising:
   a light source configured to emit at least partially coherent light toward the plurality of light scattering particles;

a photo-sensitive detector comprising one or more pixels and configured to detect light scattered off of at least some light scattering particles of the plurality of light scattering particles;

a structure adjoining the light source and the detector, the structure configured to operatively position the light source and the detector adjacent the sample, wherein the light source and the detector are positioned relative to one another at a separation distance based on an angle of projection (θ) of the light source and are configured to be positioned at a height relative to the sample such that, at the separation distance and the height, surface reflections from the sample are reduced or not detected by the detector and at least some of the emitted light scattered off of at least some light scattering particles of the plurality of light scattering particles is detected by the detector, wherein the light source and the detector are configured to be positioned approximately at the same normal distance (h) from a surface of the sample, wherein the normal distance is the height relative to the sample, wherein the light source is configured to emit the at least partially coherent light is with the angle of projection (θ) along an optical emission axis normal to the surface of the sample, and wherein the light source and detector are spaced apart along the surface by the separation distance greater than $2h \tan(\theta/2)$; and a processor operably coupled to the detector, the processor being configured to: derive a speckle contrast by at least comparing in time and/or space the light detected by the one or more pixels of the photo-sensitive detector, and determine, based on the speckle contrast, the rate of movement of the light scattering particles within the sample.

2. The system of claim 1, wherein the processor is physically coupled to the structure.

3. The system of claim 1, wherein the processor is not physically coupled to the structure.

4. The system of claim 1, wherein the processor is configured to wirelessly receive data from the detector.

5. The system of claim 1, wherein the structure is configured to maintain the light source, the detector, and the sample in a constant spatial relationship during detection.

6. The system of claim 1, wherein the speckle contrast is selected from the group consisting of: standard deviation from the mean, a median, a percent difference, a potential-well fill time difference, a gradient between pixels, and subtraction between pixels or subregions of pixels.

7. The system of claim 1, wherein the plurality of light scattering particles comprise blood cells.

8. The system of claim 1, wherein the system is configured to determine blood flow based on the rate of movement.

9. The system of claim 8, wherein the processor is further configured to determine blood circulation adequacy based on the determined blood flow.

10. The system of claim 1, wherein the structure comprises a housing containing the light source and the detector.

11. The system of claim 10, wherein the housing contains the processor.

12. The system of claim 1, wherein the structure is in the form of a patch configured to be applied to a skin surface of a subject.

13. The system of claim 1, wherein the structure further comprises an adhesive material for affixing the structure to a surface of the sample.

14. The system of claim 1, wherein the structure is configured to be coupled to the sample by means of friction.

15. The system of claim 1, wherein the structure further comprises a securing mechanism to secure the structure adjacent to a surface of the sample during detection.

16. The system of claim 15, wherein the securing mechanism is selected from a group consisting of: a spring loaded clip, a belt, and a strap.

17. The system of claim 1, wherein the structure is configured to be affixed to a region of skin of a subject.

18. The system of claim 1, wherein the structure is configured to be worn by a subject.

19. The system of claim 1, wherein the structure is in the form of a wrist band.

20. The system of claim 1, wherein the system is configured to determine the rate of movement from light scattered off at least some light scattering particles of the plurality of light scattering particles at a depth into the sample between 1 mm and 1 cm.

21. The system of claim 1, wherein the detector is selectively spaced from the light source by the separation distance that allows the detector to target light scattered from a selected depth into the sample.

22. The system of claim 1, wherein the separation distance between the light source and the detector is adjustable.

23. The system of claim 1, wherein the detector is a CMOS or CCD sensor.

24. The system of claim 1, wherein the light source is a laser.

25. The system of claim 1, wherein the light emitted by the light source is within the near-infrared spectrum.

26. The system of claim 25, wherein the light emitted by the light source is between about 700 nm and about 900 nm.

27. The system of claim 1 wherein the system is configured to place the structure in direct contact with a surface of the sample.

28. The system of claim 1, further comprising a display configured to display at least one of: an image of a detected speckle pattern, or a numerical or graphical representation of the speckle contrast, the rate of movement, a depth of penetration, or another measure derived therefrom.

29. The system of claim 28, wherein the display is adjoined to the structure.

30. The system of claim 1, wherein the detector is configured to accept unfocused light rays.

31. The system of claim 1, wherein the detector is configured to accept light paths that have not been altered by optical elements which modify the path or direction of impinging light.

32. The system of claim 31, wherein the detector is configured to accept light paths that have not been altered by lenses.

33. The system of claim 1, wherein the structure further comprises an opaque divider which is configured to limit a numerical aperture of the light source and/or the detector such that the numerical apertures of the light source and detector do not overlap on a surface of the sample.

34. The system of claim 33, wherein the opaque divider is an opaque sheet or block positioned between the light source and the detector.

35. The system of claim 33, wherein the opaque divider is an opaque housing positioned operatively in front of the detector, the opaque housing comprising an aperture for limiting the angle of detection by the detector.

36. The system of claim 1, wherein the structure is rigid along a portion between the light source and the detector.

37. The system of claim 1, wherein the one or more pixels of the detector comprise a detection area having a center and wherein the structure is configured such that an axis of peak emission of the light source is not directed at or aligned with the center of the detection area.

38. The system of claim 37, wherein the structure is configured such that the axis of peak emission is not directed at or aligned with any part of the detection area.

39. A method for determining a rate of movement of a plurality of light scattering particles within a sample, the method comprising:
positioning a structure adjacent a surface of the sample, the structure adjoining a light source configured to emit at least partially coherent light toward the plurality of light scattering particles and a photo-sensitive detector comprising one or more light-sensitive pixels and configured to detect light scattered off of at least some light scattering particles of the plurality of light scattering particles,
wherein the positioning places the light source at a first site adjacent the sample, the structure being configured to operatively position the light source at the first site relative to the sample, and
wherein the positioning further places the detector at a second site adjacent the sample, the structure being configured to position the light source and the detector relative to one another at a separation distance based on an angle of projection (0) of the light source and are configured to be positioned at a height relative to the sample such that, at the separation distance and the height, surface reflections from the sample are reduced or not detected by the detector and at least some of the emitted light scattered off of at least some light scattering particles of the plurality of light scattering particles is detected by the detector, wherein the light source and the detector are configured to be positioned approximately at the same normal distance (h) from a surface of the sample, wherein the normal distance is the height relative to the sample, wherein the light source is configured to emit the at least partially coherent light with the angle of projection (0) along an optical emission axis normal to the surface of the sample, and wherein the light source and detector are spaced apart along the surface by the separation distance greater than 2h tan(0/2),
actuating the light source, such that light is directed toward the light-scattering particles;
using the detector to detect light emitted from the light source and scattered by at least some of the light-scattering particles;
transferring signals related to the detected light from the detector to a processor; comparing, by the processor, in time and/or space the light detected by the one or more pixels of the photo-sensitive detector;
deriving, by the processor, a speckle contrast based on the comparison; and
determining, by the processor and based on the speckle contrast, the rate of movement of the light scattering particles within the sample.

40. The method of claim 39, wherein positioning the structure comprises coupling the structure to the sample.

41. The method of claim 40, wherein coupling the structure to the sample comprises coupling the structure to the sample with an adhesive material.

42. The method of claim 41, wherein coupling the structure comprises applying a patch to the skin of a user.

43. The method of claim 40, wherein coupling the structure to the sample comprises frictionally coupling the structure to the sample.

44. The method of claim 43, wherein frictionally coupling the structure comprises applying a strap, belt, or spring-loaded clip to the sample.

45. The method of claim 39, further comprising adjusting a separation distance along the structure between the light source and the detector.

46. The method of claim 39, wherein the structure is coupled adjacent to the skin of a subject.

47. The method of claim 39, wherein positioning the structure comprises placing the structure in direct contact with the surface of the sample.

48. The method of claim 39, wherein positioning the structure comprises placing the light source in substantially direct contact with a surface of the sample and placing the detector in substantially direct contact with the surface of the sample.

49. The method of claim 39, further comprising displaying at least one of: an image of a detected speckle pattern, or a numerical or graphical representation of the speckle contrast, the rate of movement, a depth of penetration, or another measure derived therefrom.

50. The method of claim 39, further comprising positioning an opaque divider before, after, or simultaneously with the positioning of the detector, wherein the opaque divider is configured to limit a numerical aperture of the light source and/or the detector such that the numerical apertures of the light source and the detector do not overlap one another on a surface of the sample.

51. The method of claim 50, wherein the opaque divider is an opaque sheet or block positioned at a third site between the first site and the second site.

52. The method of claim 50, wherein the opaque divider is an opaque housing positioned operatively in front of the detector, the opaque housing comprising an aperture for limiting the angle of detection by the detector.

53. The method of claim 39, further comprising:
selecting a depth within the sample for targeting interrogation of scattered light; and
determining the separation distance between the light source and the detector configured to target the selected depth,
wherein the first site and the second site are separated by the determined separation distance.

54. The method of claim 39, wherein using the detector to detect light comprises detecting light emitted from the light source and scattered by at least some of the light-scattering particles at a first depth within the sample, the method further comprising:
adjusting the separation distance along the structure between the light source and the detector; and
using the detector to detect light emitted from the light source and scattered by at least some of the light-scattering particles at a second depth within the sample.

55. The method of claim 39, wherein transferring signals comprises wirelessly transferring signals.

56. The method of claim 39, further comprising determining blood flow based on the rate of movement, wherein the light scattering particles comprise blood cells.

57. The method of claim 56, further comprising determining blood circulation adequacy based on the determined blood flow.

58. The method of claim 39, further comprising maintaining the light source, the detector, and the sample in a constant spatial relationship during detection.

59. The method of claim 39, wherein the speckle contrast is selected from the group consisting of: standard deviation from the mean, a median, a percent difference, a potential-well fill time difference, a gradient between pixels, and subtraction between pixels or subregions of pixels.

60. The method of claim 39, wherein using the detector to detect light comprises detecting light emitted from the light source and scattered by at least some of the light-scattering particles at a depth within the sample between 1 mm and 1 cm.

* * * * *

UNITED STATES PATENT AND TRADEMARK OFFICE
CERTIFICATE OF CORRECTION

PATENT NO. : 11,709,120 B2
APPLICATION NO. : 16/091054
DATED : July 25, 2023
INVENTOR(S) : Tyler Bywaters Rice, Sean Michael White and Bruce Yee Yang It is certified that error appears in the above-identified patent and that said Letters Patent is hereby corrected as shown below:

In the Claims

In Claim 1, Column 17, Line 10, change "projection (0)" to --projection ($\theta$)--
In Claim 1, Column 17, Line 24, change "projection (0)" to --projection ($\theta$)--
In Claim 1, Column 17, Line 28, change "2h tan(0/2)" to --2h tan($\theta$/2)--
In Claim 39, Column 19, Line 29, change "projection (0)" to --projection ($\theta$)--
In Claim 39, Column 19, Line 42, change "projection (0)" to --projection ($\theta$)--
In Claim 39, Column 19, Line 46, change "2h tan(0/2)" to --2htan($\theta$/2)--

Signed and Sealed this
Seventeenth Day of October, 2023

Katherine Kelly Vidal
*Director of the United States Patent and Trademark Office*